United States Patent [19]

Taccone

[11] 4,028,351
[45] June 7, 1977

[54] METHOD FOR THE PREPARATION OF DERIVATIVES OF SPIRO (4,5)-DECANE AND DERIVATIVES THUS OBTAINED

[75] Inventor: Ida Taccone, Voghera (Pavia), Italy

[73] Assignee: Buskine S.A., Fribourg, Switzerland

[22] Filed: Feb. 11, 1975

[21] Appl. No.: 549,061

Related U.S. Application Data

[63] Continuation-in-part of Ser. No. 445,634, Feb. 25, 1974, abandoned, which is a continuation of Ser. No. 286,752, Sept. 6, 1972, abandoned.

[30] Foreign Application Priority Data

Sept. 7, 1971 Switzerland .................... 13141/71
Feb. 12, 1974 Switzerland ...................... 2053/74

[52] U.S. Cl. .................... 260/240 K; 260/270 PD; 260/293.58; 260/293.66; 260/293.76; 260/293.78; 260/293.8; 260/293.82; 424/267
[51] Int. Cl.$^2$ ....................................... C07D 498/10
[58] Field of Search ...... 260/240 K, 293.58, 293.66

[56] References Cited

UNITED STATES PATENTS 3,655,673  4/1972  Maillard ..................... 260/293.66
3,721,675  3/1973  Maillard ..................... 260/293.62

OTHER PUBLICATIONS

Shapiro, J. Org. Chem. 15, 1027–1036, (1950).
Grob et al., Helv. Chim. Acta 41, 1184–1190, (1958).

*Primary Examiner*—G. Thomas Todd

[57] ABSTRACT

Derivatives of spiro-(4,5)-decane, are prepared from an N-substituted-4-piperidone according to a modification of the Reformatsky reaction. The N-substituted-4-piperidone is reacted in an appropriate solvent or solvent mixture with an alpha halogen ester in the presence of activated zinc. The obtained beta-hydroxy ester is reacted with an excess of hydrazine, the resultant compound being a beta hydroxy hydrazide. The latter is subjected to a Curtius transposition with nitrous acid in excess.

10 Claims, No Drawings

METHOD FOR THE PREPARATION OF DERIVATIVES OF SPIRO (4,5)-DECANE AND DERIVATIVES THUS OBTAINED

This application is a continuation in-part application of my copending application Ser. No. 445,634 filed on Feb. 25, 1974, which in turn is a Rule 60 continuation application of U.S. Ser. No. 286,752 filed on Sept. 6, 1972, both now abandoned.

This invention relates to a novel method for the synthesis of derivatives of spiro-(4,5)-decane having the general formula:

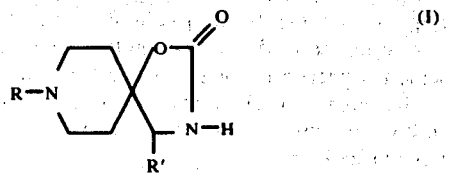

wherein R is a beta-phenyl-ethyl, 3',4'-methylene-dioxy-(beta-phenyl-ethyl), beta-(p-fluoro)-phenyl-ethyl, betaphenoxy-ethyl, cinnamyl, diphenyl-methyl, beta-(3'-trifluoromethyl)-phenyl-ethyl group, and R' is hydrogen or phenyl; and the compounds hereby obtained.

Compounds such as those listed above, in which however R'= H, or R' = an alkyl or an aryl grouping are already known in the art and more particularly in the pharmaceutical field, especially as anti-inflammatory, cough-preventing, antiasthmatic, antisecretive, cardiovascular, analgesic and tranquilizing agents.

In the British Pat. No. 1,100,281 in the name of Science Union and Cie., there are described both the compounds identified above with the formula (I) in which however, R'= H and also the methods for their preparation.

More particularly, according to the preferred method disclosed in the U.K. Patent an amino alcohol having the formula:

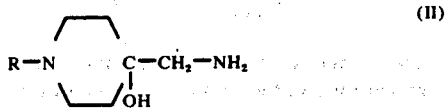

in which R has the meaning defined above and obtained by cyaniding the corresponding N-alkyl-piperidone and subsequent reduction of the thusly obtained cyanohydrin, is reacted for cyclization with urea, phosgene or an alkyl ester of carbonic acid in the presence of an alcoholate.

In the case where the nature of the substituent R makes it difficult to prepare the corresponding N-alkyl-piperidones, it is necessary to debenzylate a compound obtained according to the preceding method by converting it into a compound having the formula:

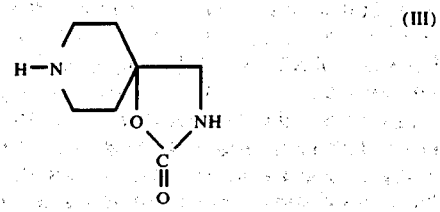

which is then caused to react with a halogenated compound R—X, wherein X is a halogen and R has the meaning specified above and is subjected to the limitation indicated at the beginning of this paragraph.

Both the above described methods are subjected to a few shortcomings and problems.

As a matter of fact, as indicated in the said U.K. Patent, the yields are not high, especially during progress of the reduction of the cyanohydrin, and undesirable by-products are present in heavy amounts.

In addition the problems and difficulties are well known which accompany the cyaniding reactions, mainly on account of the fact that highly toxic, highly volatile and difficulty removable substances are to be manipulated.

In addition, in the case of the compounds of the present invention, the introduction of substituents R' in the position shown in the formula (I) would involve, by using these prior art methods, considerable difficulties both in carrying out the reaction and in limiting and removing undesirable by-products.

There has now been found, and this is the subject matter of the present invention, a novel method for the synthesis of derivatives of spiro-(4,5)-decane having the above reported formula (I), starting from an N-substituted 4-piperidone having the formula:

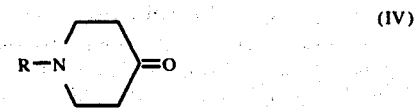

in which R' has the above stated meaning, which comprises the steps of: (I) reacting the N-substituted 4-piperidone, according to the modified Reformatsky method, in an anhydrous solvent mixture of benzene and ethyl ether and at a temperature comprised between 25° C and 70° C, with an alpha-halogen alkyl acetate having the formula:

wherein X is a halogen selected among chlorine, bromine and iodine, and R' has the aforesaid meaning in the presence of activated elemental zinc, with a molar ratio between the reagents and the zinc of at least one mole of the compound (IV), one mole of the compound (V) and one mole of activated zinc, preferably in the ratio of one mole of the compound (IV), 2.5 moles of the halogen ester and 5 moles of activated zinc, to form a beta-hydroxy-ester product having the formula:

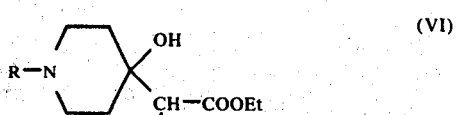

wherein R and R' are as defined above; (2) reacting the beta hydroxy ester (VI), for 8 to 30 hours and at a temperature of 40°– 60° C, with excess hydrazine, in the molar ratio of ester to hydrazine from 1: 1.5 to 1: 100, preferably 1:10, to form the corresponding beta-hydroxy-hydrazide:

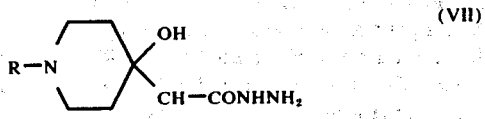

and (3) finally rearranging the beta-hydroxy-hydrazide (VII) according to the Curtius transportion reaction, by reacting it with excess nitrous acid, in the presence of a diluted mineral acid, at a temperature which ranges from room temperature to 60° C, the acidic aqueous mixture being maintained under a blanket of an organic solvent.

Another object of the present invention resides in the compounds of formula (I) in which R and R' have the above stated meanings.

The term "Reformatsky reaction" is normally intended to indicate a condensation reaction between a carbonyl compound and an ester of an alpha-halogen-aliphatic acid, in the presence of either zinc or magnesium, as described for instance by D. Shapiro in J. Org. Chem., 15, (1950), pp. 1027-1036. However the compounds of formula (I) above could not be obtained, since the reaction scheme proposed by Shapiro, if applied to N-Phenethyl-4-piperidones would mainly lead to derivatives alkylated at the piperidinic N atom.

In Helvetica Chimic Acta, vol. XLI, V (1958), No. 130, pages 1185 and following, there is described a Reformatsky reaction on 1-benzyl-4-piperidone, performed with ethyl bromoacetate and in the presence of zinc, which produced (1-benzyl-4-hydroxy-4-piperidyl)-aceto-ethyl ester, the Reformatsky method having been modified in this case inasmuch as the reaction between zinc and ethyl-bromoacetate is caused to take place prior to adding the aminoketone; the resulting ester was then separated by distillation under reduced pressure.

However, the method of the example given above, which dates back to 1958, has not been considered for the compounds having the formula (I) and for the synthesis according to the present invention, and this is because the compounds of formula (I) of the present ivention would be heavily degraded by vacuum distillation.

Considering now in detail the several stages of the method according to the present invention as defined above, the N-substituted 4-piperidone (IV) is reacted with an alpha-halogen-alkyl acetate (V). Among the possible compounds of the type R'—CH(X)—COOEt the chloro-and the bromo- and iodo-derivatives can all be used.

The most appropriate selection is a function of the form of zinc, the metal activation system, the solvents used for the reaction and the physical conditions under which the reaction is carried out. Sometimes Zn can be replaced by magnesium, the latter metal being used in a few conventional Reformatsky reactions.

As a matter of fact, magnesium, due to its high reactivity, requires a more close control of the reaction, since otherwise it could continue to react with the carboethoxy group of the obtained beta-hydroxy ester (VI).

The metal can be used as metal powder, filings, shavings, thin metal wool and can be activated in the following ways:

1. Simple washing with anhydrous organic solvents (ether, benzene, petroleum ether, acetone, etc.) and drying in vacuo at a temperature between 50° C and 120° C;

2. Treatment with diluted mineral acids, washing with prefectly neutral water, washing with acetone and subsequently with mixtures of anhydrous organic solvents and drying as in 1) above;

3. Treatment with acetone and iodine which has been twice sublimed, at elevated temperatures (40°-50° C), washing with perfectly anhydrous organic solvents and drying as in (1) above;

4. Treatment with concentrated mineral acid, either singly or in admixture (sulphuric, hydrochloric, nitric, phosphoric, etc.), washing to neutrality with water, washing with acetone and subsequently with organic anhydrous solvents and finally drying as in (1).

Among these, the method indicated at (2) is the one which is preferred for the present invention.

The reaction itself can be further improved by adding to the medium catalytic amounts of iodine or alkylmagnesium halides.

An anhydrous mixture of benzene and ethyl ether is the solvent system which is suitable for the reaction.

The complete reaction can be carried out with high yields only by operating through several steps under carefully controlled conditions, namely:

a. formation of the primary adduct

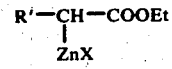

wherein R' and X have the above defined meanings, between the activated zinc and the alpha-halogen alkyl ester in a anhydrous mixture of benzene and ethyl ether until the alpha-halogen alkyl ester is wholly absent from the reaction mixture, at a temperature of between 50° and 70° C;

b. formation of the final adduct

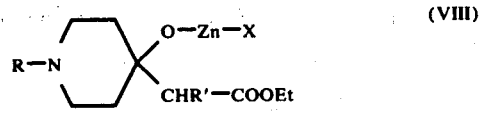

between the primary adduct and the N-substituted 4-piperidone in the same reaction medium at a temperature between 0° C and 20° C;

c. complete precipitation of the thus obtained organo-metallic adduct at a temperature of 0° C and by subsequent additions of anhydrous ethyl ether, and then separation of the organo-metallic adduct through filtration, drying and analysis thereof;

d. decomposition of the final adduct and isolation of the beta-hydroxy ester in form of an oily product tending to become solid at low temperature by means of a 50% v/v water solution of acetic acid.

In this sense the above said step is a modification of the conventional Reformatsky method. The later, if truly applied to the starting compounds of the present invention would mainly lead to the formation of undesired by-products, for instance compounds resulting from the alkylation at the piperidinic nitrogen atom and dimerization products of the carbonyl compound.

Moreover, the conventional solvents, e.g. diethyl ether, benzene, tetrahydrofuran, etc., which are normally used in the Reformatsky reaction, are not capable of a sufficient solvent action on the reaction intermediates, thus preventing the reaction from occurring plainly and the controls related to the single steps from being carried out.

The use of the mixture of benzene and ethyl ether permits the formation of the primary adduct and the further addition of the anhydrous ethyl ether permits the quantitative precipitation of the final adduct.

This obtention of a filterable precipitate is of the utmost importance since it leads to advantageous operating conditions and to improved yields.

Lastly, the decomposition of the final adduct and the isolation of the beta-hydroxy-ester are suitably carried out according to the present invention by dissolving the precipitate, after the analytical control, in a solvent mixture of acetic acid and water (in the volume ratio of 1:1). Thus, after neutralization of the resulting solution to pH 7, and extraction with an organic solvent, e.g. benzene, toluene etc., a pure beta-hydroxy-ester can be obtained, the purity of which is so high to render unnecessary any further purification steps, like distillation and so on.

The beta-hydroxy ester is subsequently converted into the beta-hydroxy-hydrazide by treatment with hydrazine either in the anhydrous form (1) or in the hydrated forms (2) (70–85% hydration).

1. The reaction is carried out by admixing the reactants in the presence (or not) of inert organic solvents such as benzene and subsequently completed either by heating the mixture at 40°–60° C during 8 – 15 hours, or by allowing the mixture to stand at room temperature during one to two weeks.

2. The reaction is carried out by admixing the reactants in the presence of inert organic solvents, such as benzene, and of alcoholic solvents, such as ethanol, so as to bring the reaction mixture always back to a homogeneous condition at high temperatures (40°– 60° C). The conversion is completed at elevated temperatures (60°–80°C) within 15 to 30 hours.

In both cases it is advisable to work with an excess of hydrazine over the stoichiometric values. The excess is intended to lie within the range from 1: 1.5 to 1: 100, preferably 1: 10.

The Curtius transposition of the intermediate leads to the formation of the final spiro-(4,5)-decane. The transposition is carried out by the action of nitrous acid, which is properly generated in situ through the reaction of an alkali metal nitrite with a diluted mineral acid, on the beta-hydroxy hydrazide. It is necessary to work in an excess of nitrous acid, the ratio of the hydrazide to the nitrous acid being at least 1: 1.6, preferably 1: 5 and over, and this excess is completely removed at the end by adding the appropriate amount of urea. The reaction is carried out by maintaining the aqueous acidic mixture under a blanket of organic solvent such as mixtures of petroleum ethers having a boiling point range of from 60° C to 90° C, temperatures which define the corresponding optimum value at which the transposition can be properly controlled and completed.

The following example illustrates in detail the application of the method of synthesis according to the present invention to the preparation of 8-N-phenethyl-1-oxa-3,8-diaza-(4,5)-decane-2-one having the structural formula:

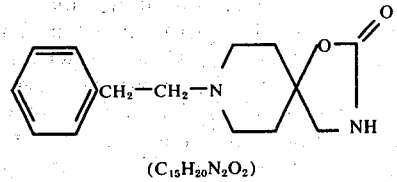

$(C_{15}H_{20}N_2O_2)$

It is fitting to indicate that the IR spectra have been recorded on a Perkin-Elmer mod. 257 apparatus. The letters in brackets, as reported beside the wavelength values, refer to the intensity of the absorption peaks; (s) = strong; (m) = medium; (w) = weak; (b) = broadened.

The thin layer chromatographies (TLC) from which the values of the front ratios ($R_F$) of the spots have been derived, have been carried out on silica gel chromatographic plates which have been activated during one hour, at 120° C, using as the eluent a mixture of chloroform/benzene/ether/methanol in the ratios 6:2:6:1 and by detecting the spots by spraying with a solution of alkalized potassium permanganate (yellow-green spots on a dark red background), the latter being obtained by admixing equal volumes of a 2% aqueous potassium permanganate solution and of a 4% solution of sodium bicarbonate.

EXAMPLE 1

A. n-phenethyl-4-hydroxy-4-ethyl acetate piperidine

A suitable flask, equipped with a column reflux condenser, electromechanical stirrer, dropping funnel and gas intake pipe, is charged with 32 grs. (0.5 mole) of activated zinc, 100 mls. of anhydrous benzene-ether mixture (1:1 v/v) and two crystals of bisublimed iodine.

At an internal temperature of 50° C, under stirring and under an inert gas blanket, the dropwise addition of a solution of 20 mls. (0.25 mole) of ethyl bromoacetate in 50 mls. of anhydrous ether-benzene mixture (1:1 v/v) is started.

After about two thirds of the charge is added, the reaction is started, the temperature begins to increase and the rate of dropping is adjusted so as to maintain the solvent under slight reflux.

At the end of the addition, the reaction mixture is refluxed during two hours and then allowed to stand for one hour.

Before starting the second step, it is necessary to check the complete disappearance of the free bromoacetic ester from the solution. To this end, a sample of the bromogeneous solution is tested by thin layer chromatography, using as the absorbent silicagel merck G 254 and as the eluent a mixture of n-hexane/chloroform in the ratio 10:2; under these conditions the ethyl bromoacetate is detected as a fluoroescent spot having $R_f$ = about 0.2.

At the same time, it also advisable to carry out a spectrophotometric control, by diluting a drop of the solution into 10 to 15 mls. of a mixture of chloroform and methanol in the ratio 1:1. The ethyl bromoacetate, under the said conditions, shows in a 1 cm. cell a strong absorption at about 238 nm.

When the absence of free bromo-ester in the reaction mixture is ascertained, the temperature is brought to about 15° C and the dropwise addition, under stirring, of a solution of 20 grs. (0.1 mole) of N-phenethyl-4-piperidone in 30 mls. of anhydrous benzene-ether (1:1)

mixture is started. During the addition it is advisable to add to the reaction mixture further amounts of 10–20 mls of ether, in order to promote the separation of the final product, in form of a solid well dispersed the solvent. At the end of the said addition, the suspension is further vigorously stirred at 0° C during 2 hours.

The aforedescribed technique permits the several controls of the reaction to be effected with high precision and, therefore, to obtain high yields of pure product, which is not effected by undesired reaction by-products.

The end of the reaction is detected by thin layer chromatography by checking both the disappearance of the spot indicating the starting N-phenethyl-4-piperidone and the appearence of the more polar spot having Rf=0.3.

The final reaction product is isolated by conventional filtering techniques and then dried under vacuum at 40° – 50° C.

Before carrying out the hydrolysis of the reaction product, the following controls are effected:

Dosing of the zinc with ethylenediaminetetra-acetic acid (EDTA)
Acidimetric titration
Chromatography.

The solid reaction product, having the formula

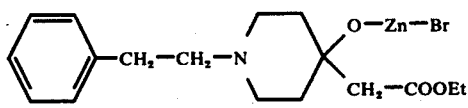

is hydrolyzed in a mixture of acetic acid-water (1:1 v/v) under stirring at low temperature.

Once the product is completely dissolved, the solution is neutralized at pH 7 by means of 20% w/v $NH_4$ OH, the temperature being maintained at 0° C. The solution is then extracted several times with 100 ml portions of benzene.

The combined benzene extracts are dried over anhydrous $K_2 CO_3$, filtered and concentrated up to a fixed residue.

The residue (20 grs. namely 70% of the theoretical mole yield) shows the following properties:
TLC : $R_f$ = 0.3 approx.
IR (liquid film). Peaks at:

| 3200–3700 cm$^{-1}$ | (b) $\nu$–OH |
| 1730 cm$^{-1}$ | (s) $\nu$C = 0 of –O–CO–R |
| 700 cm$^{-1}$ | (m) } with aromatic |
| 750 cm$^{-1}$ | (m) } substitution |

NMR (Cd Cl$_3$):
—triplet centered at 1.5 δ(ppm) =

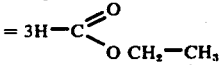

—quadruplet centered at 4.4 δ(ppm) =

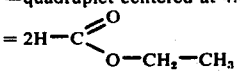

Treatment with thionyl chloride, in order to assess the presence of the beta-hydroxy ester group.

The test is simultaneously carried out in two test tubes. To a solution of 0.5 ml of beta-hydroxyester in 1 ml. benzene there is added 1 ml. of SOCl$_2$. One of the two samples is allowed to stand 15 minutes at room temperature, whereas the second is kept on a water bath at about 75° C undisturbed for 15 minutes. Once the prescribed time has elapsed, each of the two solutions is treated with 2mls. of water, the whole is passed into a separatory funnel and the resultant aqueous phase is made alkaline by addition of ammonium hydroxide and repeatedly extracted with 2–3 ml. portions of benzene. The combined benzene solutions are thoroughly salted out, washed with water to neutrality, dried over K$_2$CO$_3$ and concentrated in vacuo. The resultant samples have the following chromatogram:

a. Room temperature test. Spots with $R_f$ = 0.3; 0.5; 0.6
b. Tests at 75° C. Spots with $R_f$ = 0.5; 0.6;

B. N-phenethyl-4-hydroxy-4-acetohydrazide piperidine

A 500 ml. flask equipped with a reflux stirrer is charged with 20 grs. (0.07 mole approx.) of N-phenethyl-4-hydroxy-4-ethyl acetate piperidine dissolved in 20 mls. benzene. To the solution there is added a strong excess of hydrazine hydrate (30 mls. of the 85% reagent-0.6 mole approx.) and the resultant mixture is heated to a temperature of about 50° – 60° C. Ethyl alcohol is then added until obtaining a homogeneous solution in hot conditions. The mixture is maintained at 50° – 60° C during one hour and then is brought back to room temperature again, and allowed to stand for five days. On completion of the reaction, the excess hydrazine is removed under vacuum in a desiccator over H$_2$SO$_4$ and subsequently the solution is evaporated to dryness still in vacuo, a brown solid product being obtained with a yield of 75 – 85% of theory on a weight basis. The beta hydroxy hydrazide, as crystallized from diethyl ether has the following specifications:

Melting point : 110° C (not corrected)
TLC : $R_f$ = O approx. IR (in nujol) Bands at:

| 3200 cm$^{-1}$ | (b) $\nu$–OH |
| 3380 cm$^{-1}$ | (m) $\nu$–NH of –CONHNH$_2$ |
| 3300 cm$^{-1}$ | (m) $\nu$–NH of –CONHNH$_2$ |
| 1650 cm$^{-1}$ | (s) $\nu$– C = 0 of –CONHNH$_2$ |
| 750 cm$^{-1}$ | (m) } monosubstituted aromatic |
| 700 cm$^{-1}$ | (m) } |

C. 8 N-phenethyl-1-oxa-3,8-diaza-spiro (4,5) decane-2-one

In a 1,000 ml. flask there are dissolved 25 grs. of beta hydroxy hydrazide in 150 mls. 2N HCl and the solution is blanketed with a layer of petroleum ether (b.p. 65° – 90° C). In the reaction vessel, which has been previously cooled at 5° – 10° C, an aqueous solution of an excess of sodium nitrite (about 10 grs. of the salt in 100 mls. water) is added dropwise.

On completion of the addition, the nitrous acid which is present is decomposed with urea (about 5 grs.), a reflux condenser is applied to the flask and heat is gently applied, while maintaining the stirring. Even at room temperature nitrogen evolution can be observed, an evolution which becomes vigorous at 50° – 60° C. The reaction is exothermic and the refluxing of the petroleum ether layer is intended to absorb the built up heat. Once the nitrogen evolution has been terminated, the mixture is cooled, poured in a separatory funnel and the acidic aqueous phase is collected. The latter is made alkaline by addition of concentrated ammonium hydroxide, thoroughly salted out and extracted several times with benzene. The benzene extract is washed to neutrality, dried over $K_2CO_3$ and the solvent is evaporated under vacuum. The obtained spiro decane (mole yield: 80% of theory) crystallizes from benzene/petroleum ether and has the following specifications:

Melting point 154°–156° C
TLC : $R_f = 0.1$
UV in methanol $\lambda_{max} = 258$ nm
IR (in nujol) Bands at:

| | |
|---|---|
| 3280 cm$^{-1}$ | (m) $\nu$—NH |
| 1730 cm$^{-1}$ | (s) $\nu$—C = O of —O—CO—NH— |
| 750 cm$^{-1}$ | (m) ⎫ monosubstituted aromatic |
| 700 cm$^{-1}$ | (m) ⎭ |

The final molar yield of the steps A, B and C as a whole, is 41.6% of theory, referred to the starting piperidone-4.

In the following Examples 2 to 9, the same process of Example 1 has been repeated, except that the starting N-substituted 4-piperidone was different.

EXAMPLE 2

1-oxa-2-oxo-3,8-diaza-8 (3',4'-methylenedioxy-phenethyl)-spiro-(4,5)-decane-

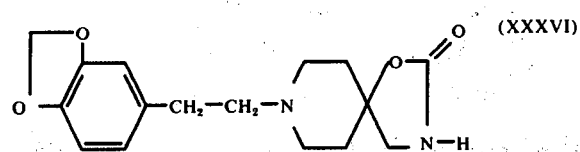

m.p. : 183° C
The starting 1-(3',4'-methylenedioxy-phenethyl)-piperidone-4

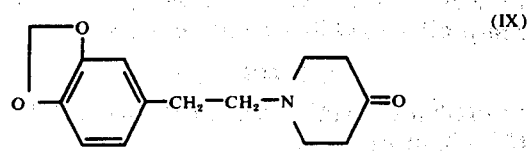

is prepared by alkylating piperidone-4 with 3,4-methylenedioxy-phenethyl chloride. The preparation of the beta-hydroxy-ester is carried out by reacting, according to the Reformatsky modified technique, the compound (IX) with ethyl bromo-acetate.

The mole yield of the compound (XXXVI), as free base, is 24% of theory, with respect to the starting piperidone-4 (IX).

EXAMPLE 3

1-oxa-2-oxo-3,8-diaza-8(4'-fluorophenethyl)-spiro(4,5)-decane

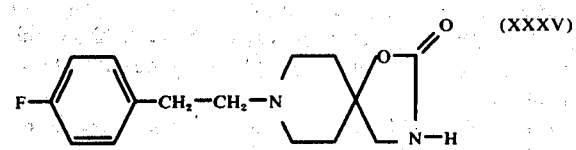

Melting point: a) free base = 152° C; b) hydrochloride = 247° C.
The starting 1-(4'-fluorophenethyl)-piperidone-4 (X)

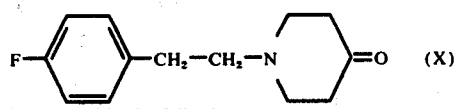

is prepared in the following way

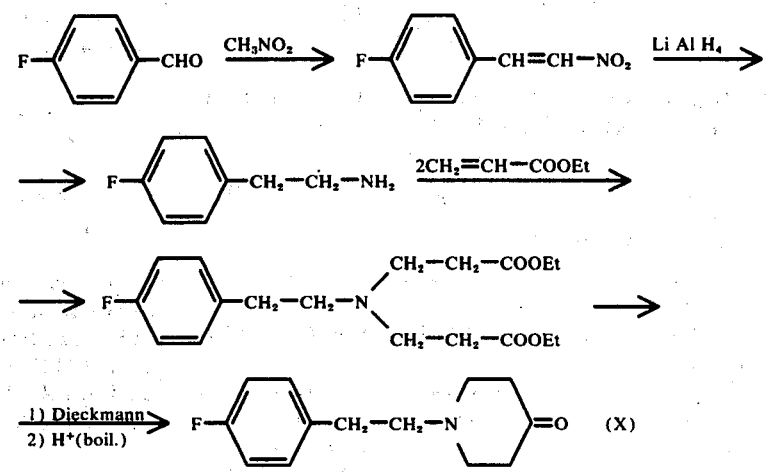

The beta-hydroxy ester is prepared by reacting, according to the modified Reformatsky reaction, the compound (X) with ethyl bromoacetate.

The molar yield of the compound (XXXV), as free base, is 46% of the theory, referred to the starting piperidone-4.

EXAMPLE 4

1-oxa-2-oxo-3,8-diaza-8-phenoxyethyl-spiro(4,5)-decane

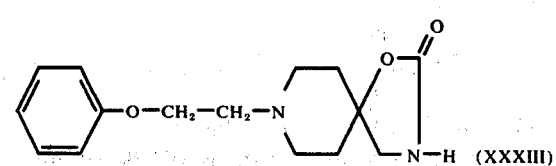

Melting point: a) free base = 138° C; b) hydrochloride = 226° C

The starting 1-phenoxyethyl piperidone-4 (XI)

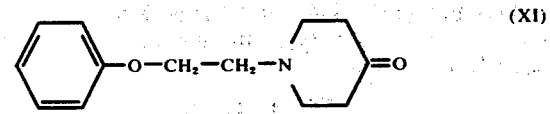
(XI)

is prepared by alkylating the piperidone-4 with phenoxyethyl bromide.

The preparation of the beta-hydroxy ester is carried out through the reaction of the compound (XI) with ethyl bromoacetate, according to the modified Reformatsky technique.

The mole yield, as free base, of the compound (XXXIII) is 55% of theory, referred to the starting piperidone-4 (XI).

EXAMPLE 5

1-oxa-2-oxo-3,8-diaza-8-cinnamyl-spiro(4,5)-decane

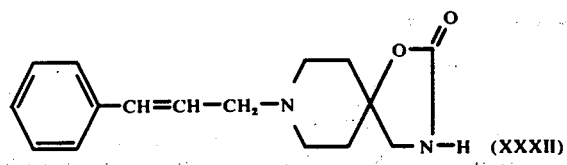
(XXXII)

Melting point of the free base: 176° C. The starting 1-cinnamylpiperidone-4 (XII)

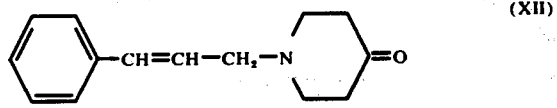
(XII)

is prepared by alkylating piperidone-4 with cinnamyl chloride.

The modified Reformatsky reaction is carried out on the compound (XII) by means of ethyl bromoacetate, leading to the corresponding beta-hydroxy-ester.

The mole yield of the compound (XXXII), as free base, is 31% of theory, referred to the starting piperidone.

EXAMPLE 6

1-oxa-2-oxa-3,8-diaza-8-diphenylmethyl-spiro(4,5)-decane

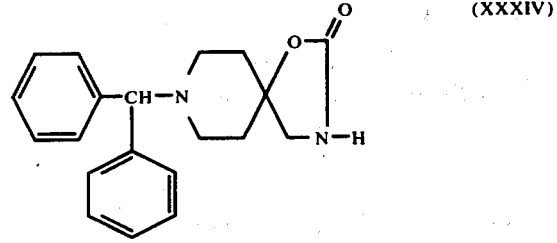
(XXXIV)

Melting point of the free base : 200° C.

The starting 1-diphenylmethyl piperidone-4 (XIII)

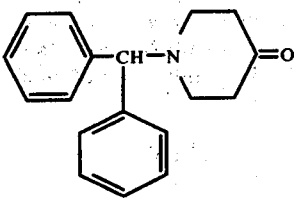
(XIII)

is prepared by alkylating piperidone-4 with diphenyl methyl bromide.

The modified Reformatsky reaction is carried out on the compound (XIII) with ethyl bromoacetate.

The mole yield of the compound (XXXIV) is 34% of theory, referred to the starting piperidone-4.

EXAMPLE 7

1-oxa-2-oxo-3,8-diaza-8(3'-trifluoromethyl-phenethyl)-spiro(4,5)-decane

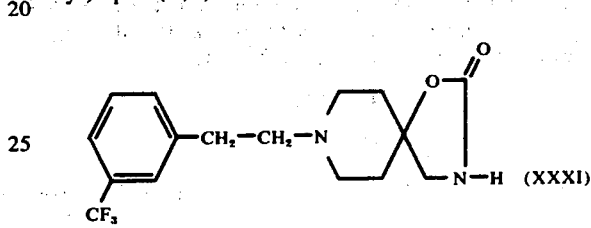
(XXXI)

Melting point of the hydrochloride: 232° C.

The starting 1-(3'-trifluoromethyl-phenethyl) piperidone-4-(XIV)

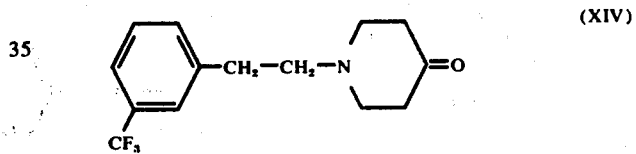
(XIV)

is prepared from n-trifluoromethyl benzaldehyde as shown in Example 2.

The modified Reformatsky reaction on the compound (XIV) is effected with ethyl bromoacetate. The mole yield of the compound (XXXI) is 60% of theory, referred to the starting piperidone-4.

EXAMPLE 8

1-oxa-2-oxo-3,8-diaza-8-benzyl-spiro(4,5)-decane

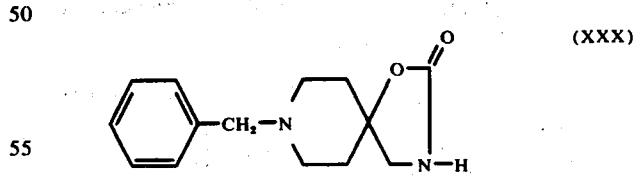
(XXX)

Melting point of the free base = 178° – 179° C. The starting 1-benzyl piperidone-4 is an easily available chemical product.

The modified Reformatsky reaction is carried out by means of ethyl bromoacetate.

The mole yield of the compound (XXX) is 80% of theory, referred to the starting piperidone.

EXAMPLE 9

1-oxa-2-oxo-3,8-diaza-8-phenethyl-1-4-phenyl-spiro(4,5)-decane

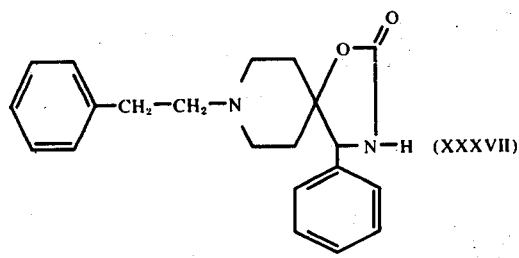

Melting point: 211° C
The starting 1-phenethyl-piperidone-4(XV)

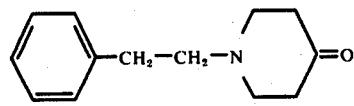
(XV)

is prepared according to the following scheme:

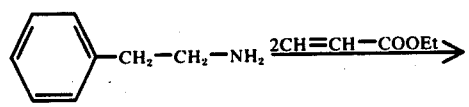

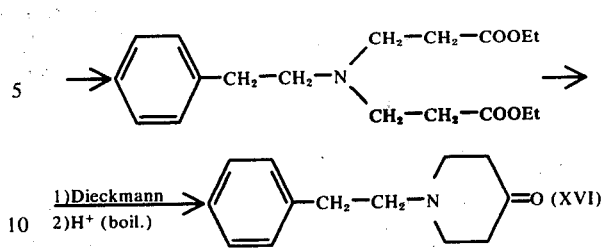

The modified Reformatsky reaction is effected by reacting the compound (XVI) with ethyl bromophenylacetate. The mole yield of the compound (XXXVII) is 31% of theory, referred to the starting piperidone.

In the preceding Examples the modified Reformatsky reaction was carried out with ethyl bromo-acetate, but this is not to be taken as a limitation, since the choice is only dependent on the fact that a five-membered ring is to be formed.

In the following table 1 some results of pharmacological tests are reported, confirming the stated interesting properties of the claimed compounds.

TABLE 1

| | | BRONCHO-SPASM 50% approx. inhibiting dose mg/kg i.v. | | | HEATED PLATE TEST (mouse) | | KAOLIN INDUCED OEDEMA (rat) | |
|---|---|---|---|---|---|---|---|---|
| R= | LD$_{50}$ (rat) mg/kg i.p. | Histamine | Serotonine | Acetylcholine | i.p. mg/kg | % increase of threshold value | Total dose mg/kg per os (48 hours) | Volume variation % |
| R= ⟨benzodioxole⟩-CH$_2$-CH$_2$- | 235 (196-282) | 0.2 | >2.5 | >2.5 | 40 | 80 | 310 | 39.5 ↓ |
| R= F-⟨phenyl⟩-CH$_2$-CH$_2$- | 282 (256-312) | 0.2 | 0.5 | 2 | 10 | 41.7 | 70 | 19.4 ↓ |
| R= ⟨phenyl⟩-O-CH$_2$-CH$_2$- | 344 (323-365) | >0.5 | >0.5 | >0.5 | 100 | 49 | 440 | 26.3 ↓ |
| R= Ph-CH(Ph)- | 346 (325-368) | >0.5 | >0.5 | >0.5 | 100 | 119 | 440 | 4.6 ↓ |
| R= CF$_3$-⟨phenyl⟩-CH$_2$-CH$_2$- | 344 (286-412) | 0.5 | >0.5 | >0.5 | 50 | 45.6 | 310 | 10 ↓ |
| R= ⟨phenyl⟩-CH$_2$- | 319 (330-339) | >0.5 | >0.5 | >0.5 | 100 | 93 | 340 | 9.4 ↓ |

TABLE 1-continued

| | | BRONCHO-SPASM 50% approx.inhibiting dose mg/kg i.v. | | HEATED PLATE TEST (mouse) | | KAOLIN INDUCED OEDEMA (rat) | |
|---|---|---|---|---|---|---|---|
| 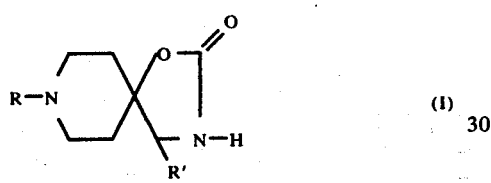 | LD₅₀ (rat) mg/kg i.p. | Histamine | Sero-tonine | Acetyl-choline | i.p. mg/kg | % increase of threshold value | Total dose mg/kg per os (48 hours) | Volume variation % |
| R= 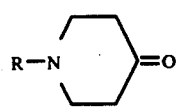 —CH₂—CH₂— | 230 (198-266) | 0.5 | 0.2 | 2 | 25 | 63.4 | 190 | 16.1 |

In the preceding Table 1:
a) the data of analgesic activity are expressed as the variation % of the stimulation threshold in the mouse;
b) the data of anti-inflammatory activity are expressed as the volume variation of the kaolin induced oedema in the Wistar rat;
c) the experiments on the antagonist activity against the bronochospasm were carried out on guinea pigs, according to the technique taught by Konzett and Roessler (Arch Exper. Pathol. Pharm.,71, (1940), 195).

What I claim is:
1. A method for the preparation of a spiro-[4,5]-decane derivative having the formula:

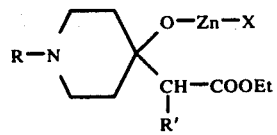

(I)

in which R is selected from the group consisting of beta-phenylethyl, 3',4'-methylenedioxy (beta-phenylethyl)-, beta-(p-fluoro)-phenyl-ethyl; beta-phenoxyethyl, cinnamyl, diphenyl-methyl, and beta-(3'-trifluoromethyl)-phenyl- ethyl, and R' is hydrogen or phenyl, which comprises the steps of:
1. reacting, at a temperature of between 50° and 60° C, an alpha-halogen alkyl acetate, having the formula R'—CH—COOEt
|
X wherein R' is as defined above and X is Cl, Br or I, in the presence of activated elemental zinc to form a primary adduct having the formula R'—CH—COOEt
|
ZnX wherein R' and X have the above defined meanings, in an anhydrous solvent mixture of benzene and ethyl ether, until the alpha-halogen alkyl ester is wholly absent from the reaction mixture;
2. adding at least one mole of an N-substituted-4-piperidone of the formula

where R is as defined above per mole of primary adduct in the reaction mixture from step (1) at a temperature between 0° and 20° C. to form a final adduct, having the formula

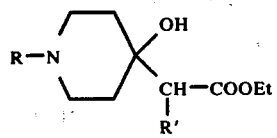

3. completely precipitating the final adduct at a temperature of 0° C by stepwise addition of anhydrous ethyl ether, and separating the final organo-metallic adduct by filtering and drying;
4. decomposing the solid final adduct with water to form an oily beta-hydroxy ester product of the formula

wherein R and R' are as defined above;
5. neutralizing the reaction mixture from step (4) to pH 7; extracting the beta-hydroxy ester product with an organic solvent and isolating the beta-hydroxy ester;
6. reacting said beta-hydroxy ester product with excess hydrazine for 8 to 30 hours at a temperature of 40°-60° C, in the molar ratio of ester to hydrazine of 1:1.5 to 1:100, to form the corresponding beta-hydroxy-hydrazide, having the formula

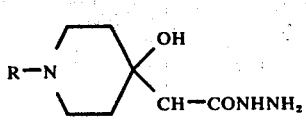

and (7) rearranging said beta-hydroxy hydrazide, according to the Curtius transportion reaction, by reacting it with excess nitrous acid, in the presence of a diluted mineral acid at a temperature from room temperature to 60° C, to form the spiro [4,5]-decane derivative of formula (I).

2. The method of claim 1, wherein the mole ratio of N-substituted piperidone to alpha-halogen alkyl acetate to activated elemental zinc in step (1) is 1 : 2.5 : 5.

3. The method of claim 1, wherein the reaction of step (2) is carried out until, on analyzing the reaction mixture, the absence of the N-substituted 4-piperidone is checked.

4. The method of claim 1, wherein the decomposition of the final adduct in step (4) takes place by hydrolysis carried out with a mixture of acetic acid and water in the volume ratio of 1:1.

5. The method of claim 1, wherein the reaction medium of step (1) is an anhydrous mixture of benzene and ethyl ether in the volume ratio of 1 : 1.

6. The method of claim 1, wherein the ratio of the betahydroxy ester product to hydrzine in step (6) is 1 to 10, and the ratio of hydrazide to nitrous acid in step (7) is 1 : 1.6.

7. The method of claim 1, wherein step (7) is carried out under a blanket of petroleum ethers having a boiling point between 60° C and 90° C.

8. 1-oxo-2-oxa-3,8-diaza-8-phenoxyethyl-spiro-decane.

9. 1-oxa-2-oxo-3,8-diaza-8-cinnamyl-spiro decane.

10. 1-oxa-2-oxo-3,8-diaza-8-diphenylmethyl-spiro-decane.

* * * * *